United States Patent
Sachs et al.

(10) Patent No.: US 7,259,145 B2
(45) Date of Patent: Aug. 21, 2007

(54) MECHANICALLY ACTIVATED CHANNEL BLOCKER

(75) Inventors: Frederick Sachs, Eden, NY (US); Thomas Suchyna, Amherst, NY (US); Phillip Gottlieb, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 95 days.

(21) Appl. No.: 11/176,745

(22) Filed: Jul. 7, 2005

(65) Prior Publication Data

US 2006/0014691 A1  Jan. 19, 2006

Related U.S. Application Data

(60) Provisional application No. 60/585,895, filed on Jul. 7, 2004.

(51) Int. Cl.
*A61K 38/16* (2006.01)
*C07K 14/00* (2006.01)

(52) U.S. Cl. .......................... 514/12; 530/324; 530/858

(58) Field of Classification Search ..................... None
See application file for complete search history.

(56) References Cited

U.S. PATENT DOCUMENTS

| 5,756,663 A | 5/1998 | Lampe et al. |
| 6,261,569 B1 | 7/2001 | Comis et al. |

FOREIGN PATENT DOCUMENTS

| WO | WO 01/76618 | 10/2001 |
| WO | WO 2004/085647 | 10/2004 |

OTHER PUBLICATIONS

Suchyna, Thomas M. et. al., Bilayer-dependent inhibition of mechanosensitive channels by neuroactive peptide enantiomers; Nature, vol. 430 (6996) Jul. 8, 2004, pp. 235-240.

Gottlieb, Philip A., et. al., Mechanosensitive Ion Channels as Drug Targets; Current Drug Targets, CNS & Neurological Disorders, vol. 3 (4), Aug. 2004, p. 287-295.

*Primary Examiner*—Jeffrey Edwin Russel
(74) *Attorney, Agent, or Firm*—Hodgson Russ LLP

(57) ABSTRACT

The present invention discloses a peptide of SEQ ID NO:1 and its variants that blocks stretch-activated ion channels. All amino acids in this peptide are D-amino acids. The peptide, designated as D-GsMTx4, is an enantiomer of a peptide GsMTX-4 present in the venom of the spider *Grammostola spatulata*. The present invention also discloses a method for inhibition of stretch activated ion channels in a cell. This peptide can be used for the treatment of cardiac arrhythmias and other pathologies that involve alterations in mechanical stress.

11 Claims, 4 Drawing Sheets

SEQUENCE LISTING

<160> NUMBER OF SEQ ID NOS: 1

<210> SEQ ID NO 1
<211> LENGTH: 34
<212> TYPE: PRT

```
<213> ORGANISM: Artificial Sequence
<220> FEATURE:
<223> OTHER INFORMATION: D-enantiomer of peptide from Grammostola
      spatulata

<400> SEQUENCE: 1

Gly Cys Leu Glu Phe Trp Trp Lys Cys Asn Pro Asn
                  5                   10

Asp Asp Lys Cys Cys Arg Pro Lys Leu Lys Cys Ser
            15                  20

Lys Leu Phe Lys Leu Cys Asn Phe Ser Phe
 25                  30
```

MECHANICALLY ACTIVATED CHANNEL BLOCKER

This application claims priority to U.S. provisional application No. 60/585,895 filed on Jul. 7, 2004, the disclosure of which is incorporated herein by reference.

FIELD OF THE INVENTION

The present invention relates to the field of stretch-activated channels. More particularly the present invention provides peptides comprising D-amino acids that block stretch-activated channels, such as those associated with cardiac arrhythmias.

DISCUSSION OF RELATED ART

Cardiac fibrillation is a frequent cause of sudden death. Atrial fibrillation is the most common sustained cardiac arrhythmia to occur in humans, second only to valve disease, hypertension, or heart failure. Atrial fibrillation is often associated with passive stretching of the arterial chamber arising from haemodynamic or mechanical dysfunction of the heart. It has been suggested that abnormal mechanical factors induce electrophysiological changes conducive to arrhythmia via "mechanoelectric feedback". Stretch-activated channels (SACs) have been postulated as a mechanism of mechanoelectric feedback and they may play a role in the genesis of cardiac arrhythmias.

Mechanosensitive ion channels (MSCs), of which SACs are an example, were discovered in tissue cultured skeletal muscle cells using single channel patch clamp recordings. They have since been found in both the plant and animal kingdoms and in the cells of most tissues, including myocardial tissue. Most of them open with increasing membrane tension (stretch-activated channels (SACs)), but a few are tonically active and close with increasing tension (stretch-inactivated channels (SICs)). It is now well recognized that myocardial stretch can cause arrhythmias due to stretch-induced depolarizations.

SACs have been implicated as either activators or modifiers of many different cellular responses to mechanical stimuli including modification of electrical and contractile activity of muscle tissue. Consequently, SACs have been implicated in mechanical sensitivity of the heart. Mechanical stimulation of cardiac myocytes and whole heart preparations can cause depolarization, extrasystoles and arrhythmias (Hu et al., 1997; *J Mol Cell Cardiol* 29:1511-1523). Also, chronic hemodynamic stress that leads to congestive heart failure (CHF) and the accompanying cellular hypertrophy may be initiated by stretch-or swelling-activated currents (Sachs, 1988; *Crit Rev Biomed Eng* 16:141-169; Vandenberg et al., 1996; *Cardiovasc Res* 32:85-97; Clemo et al., 1997; *J Gen Physiol* 110:297-312).

SACs are the only major class of ion channels for which a specific inhibitor is not known. $Gd^{3+}$ is the best known blocker of SACs ($K_D$'s ranging from 1-100 mM) and is widely used to identify these channels. However, $Gd^{3+}$ also blocks a variety of other channels such as L-and T-type $Ca^{2+}$ (Biagi et al., 1990, *Am. J. Physiol.*, 264:C1037-1044), $K^+$ delayed rectifier, voltage-gated $Na^+$ (Elinder et al., 1994, *Biophys. J.*, 67:71-83) and $Ca^{2+}$ ER release channels (Kluesener et al., 1995, *EMBO J.*, 14:2708-2714). A variety of blockers for voltage-and ligand-gated channels (e.g. amiloride, cationic antiobiotics, tetrodotoxin, tetraethylammonium, quinidine, diltiazem and verapamil) exhibit low affinity blocking activity against SACs (for review see Hamill et al., 1996, *Pharmacol Rev* 48:231-252; Sachs et al., 1998; Blaustein, R. Greger, H. Grunicke, r. Jahn, L. M. Mendell, A. Miyajima, D. Pette, G. Schultz, and M. Schwieger, editors; Springer, Berlin 1-78).

Thus, while several studies point to a role for SACs in mechanical sensitivity, a lack of specific SAC agents has hampered the development of SAC based approach to the treatment of arrhythmias. The peptide GsMTx4, isolated from the venom of the tarantula *Grammostola spatulata*, is a selective inhibitor of stretch activated cation channels (SACs). However, the usefulness of this peptide for human use has not yet been established, although the peptide would appear to be non-toxic. While GsMtx4 is somewhat resistant to proteolysis, reducing the proteolyis rate will aid pharmacokinetic retention, useful for cardiac therapy. Consequently, there is an ongoing need to identify agents that can block SACs and can be clinically useful as anitarrhythmic agents.

SUMMARY OF THE INVENTION

The present invention discloses an enantiomer of a peptide, whose L form is present in the venom of the spider *Grammostola spatulata*. This peptide blocks stretch-activated ion channels. The peptide is designated as GsMTx4. The enantiomer of this peptide is designated herein as D-GsMTx4. The amino acid sequence of this peptide is disclosed in SEQ ID NO:1. The L-form of GsMTx-4 peptide is referred to herein as GsMTx4 or as the wild type GxMTx4 or L-GsMTx4.

The present invention also provides a method for inhibition of stretch activated ion channels in a cell. The method comprises the step of applying to the cell a sufficient amount of the peptide D-GsMTx4.

The present invention also provides a method for the treatment of cardiac arrhythmias. The method comprises the step of applying the peptide D-GsMTx4 to a heart tissue that is exhibiting arrhythmia.

DETAILED DESCRIPTION OF THE INVENTION

Figure 1:
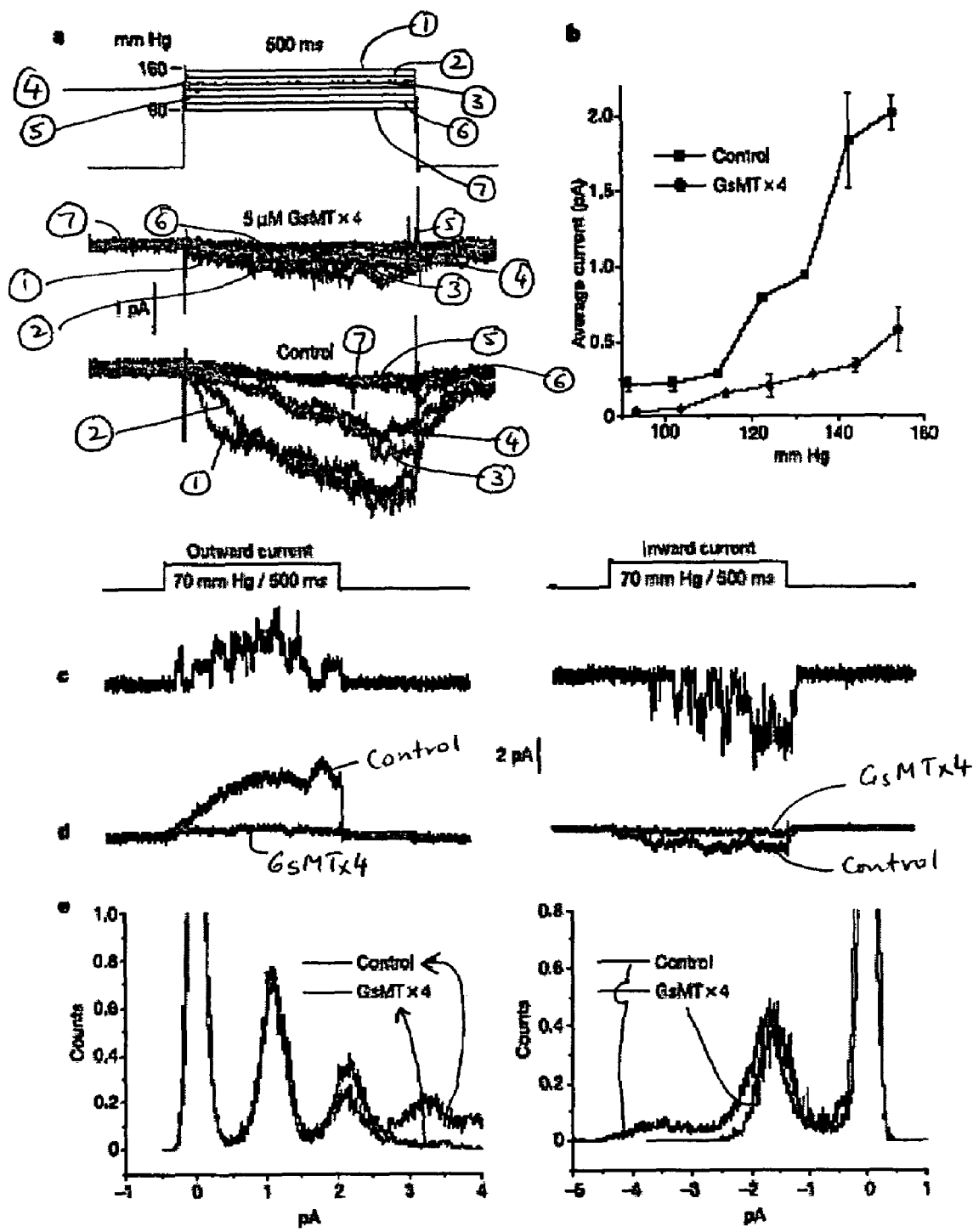
FIG. 1 is a representation of the effect of GsMTx4 on the pipette pressure (membrane tension) required for activation and is adjacent to the channel. a, Ensemble-averaged SAC currents from a single outside-out astrocyte patch in the absence and presence of 5 μM GsMTx4; b, Average patch currents as a function of pressure in the absence and presence of 5 μM GsMTx4 (2 patches, mean ^ s.e.m.); c, shows single-channel currents from a chick heart cell, the outside-out patch in the absence of GsMTx4; d, average currents in the chick heart cell outside-out patch. Control (black trace) and 5 mM GsMTx4 (red trace); e, Histograms of unitary current amplitude (left) (Þ150 mV pipette potential: control, 1.10 pA; 5 mM GsMTx4, 1.08 pA), (right) (250 mV pipette potential: control, 1.74 pA; 5 mM GsMTx4, 1.58 pA).

The present invention discloses enantiomers of a peptide, whose L form is present in the venom of *Grammostola spatulata*. The peptide has the following sequence.

GCLEFWWKCNPNDDKCCRPKLKC-
SKLFKLCNFSF-amide-(SEQ ID NO.1)

In the present invention, one or more L-amino acids were replaced by D-amino acids. In one embodiment, all the amino acids were replaced by D-amino acids. This peptide is designated herein as D-GsMTx-4. This peptide contains six cysteine residues and does not show significant homology to any other peptide toxin.

In a co-pending application we have shown that variants of the GsMTx4 also has channel blocking activity. In this application we show that the D enantiomer of this peptide also has channel blocking activity. It will be apparent to those skilled in the art that variants of D-GsMTx4 may also have channel blocking activity. Thus, variants of D-GsMTx4 which have channel blocking activity are also included within the scope of the present invention The term "Variants" of the peptide for the purposes of specification and claims means peptides which have substitutions, additions or deletions in the sequence of SEQ ID NO:1 such that the resulting peptide, having at least one D-amino acids is resistant to proteolysis, exhibits SAC blocking activity and has a sequence which can form an inhibitor cysteine knot (therefore has an ICK motif).

Variants of the present invention include conservative substitutions of one hydrophobic residue for another, or the substitution of one polar residue for another such that the resultant peptide is capable of blocking SACs, Examples of conservative substitutions include the changes of: alanine to serine; arginine to lysine; asparagine to glutamine or histidine; aspartate to glutamate; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. Those skilled in the art will also recognize that variants of the peptide can be made by addition or deletion of amino acids.

The peptides of the present invention have a structure determined from the sequence and NMIR data, that show it to have 6 cysteines that form an inhibitory cysteine knot (the ICK motif). This motif is formed by 3 disulfides, which has one disulfide threaded through an embedded ring formed by the other two (for review see: Pallaghy, et.al., 1994. Protein Sci 3:1833-1839; Norton, R. S. & P. K. Pallaghy, 1998. Toxicon 36: 1573-1583; Daly, N. L. & D. J. Craik. 2000. J Biol Chem 275: 19068-19075). This is a common toxin motif used by a variety of species including fungi, plants, marine mollusks, insects and spiders. While not intending to be bound by any particular theory, the multiple disulfide bonds of the ICK motif fold small peptides into compact structures that are somewhat resistant to enzymatic digestion and form a useful rigid scaffold for presentation of more flexible interacting groups. The key residues generally reside at the outer surface. GsMTx4 does not show >50% homology to any other published peptide toxin sequence. Other tarantula peptides which block voltage gated $Ca^{2+}$ and $K^+$ channels show the highest percentage of similarity to GsMTx4.

The peptide GsMTx4 and its variants can be prepared by chemical synthesis using automated or manual solid phase methods. Such technologies are well known in the art. For example, such technologies are described in E. Atherton and R. C. Sheppard, Solid Phase Peptide Synthesis: A Practical Approach, IRL Press/Oxford Univeristy Press, Oxford, England, 1989; and M. Bodanzky, Peptide Chemistry: A Practical Textbook, Springer-Verlag, New York, N.Y., 1988. Thus, the peptide GsMTx-4 can be synthesized using Fmoc chemistry or an automated synthesizer. Depending upon quantitative yields, production of the linear reduced peptide can be performed in either a single process or in two different processes followed by a condensation reaction to join the fragments. A variety of protecting groups can be incorporated into the synthesis of linear peptide so as to facilitate isolation, purification and/or yield of the desired peptide. Protection of cysteine residues in the peptide can be accomplished using protective agents such as triphenylmethyl, acetamidomethyl and/or 4-methoxybenzyl group in any combination.

The peptide D-GsMTx4 of the present invention can be prepared for pharmaceutical use by incorporation with a pharmaceutically acceptable carrier or diluent. The peptide can be formulated into tablets, capsules, caplets and the like. Suitable carriers for tablets include calcium carbonate, starch, lactose, talc, magnesium stearate and gum acacia. The peptide can also be formulated for oral, parenteral or intravenous administration in aqueous solutions, aqueous alcohol, glycol or oil solutions or emulsions. The peptide can also be formulated for inhaling by encapsulating to facilitate alveolar absorption as has been done for insulin (Inhale Therapeutic Systems, San Carlos, Calif., www. Inhale.com). Pharmaceutical compositions suitable for such routes of administration are well known in the art. For example, suitable forms and compositions of pharmaceutical preparations can be found in Remington's Pharmaceutical Science, 1980, 15[th]ed. Mack Publishing Co., Easton, Pa. Thus, the peptide GsMTx4 can be administered orally, parenterally, intravenously, intramuscularly or intranasally. The peptide may also be applied to the tip of a catheter or other devices coming into contact with the heart during invasive procedures.

Those skilled in the art will recognize that the dosage administered to a particular individual will depend on a number of factors such as the route of administration, the duration of treatment, the size and physical condition of the individual, and the patient's response to the peptide including the side effects. Antiarrhythmic concentrations of another peptide toxin from spider venom are disclosed in U.S. Pat. No. 5,756,663. As used herein the antiarrhythmic activity refers to the activity of the peptide GsMTx-4 in blocking stretch-activated channels in myocytes. Additionally, the present peptide can also be used for its effect on SACs in other pathological or non-pathological conditions. For example, it can be used in muscular dystrophy, glial tumors and incontinence (Ostrow et al., *Brain Research Reviews* 48, 488-508, 2005; Gottlieb et al., *Current Drug Targets—CNS & Neurological Disorders* 3, 287-295, 2004; Tertyshnikova et al., *J Urol.* 169, 756-760, 2003).

In this invention it was observed that the D-form of the peptide has equivalent efficacy to the wild type L-form. The surprising efficacy of the D form of GsMTx4 peptide has important therapeutic implications, because D peptides are not hydrolyzed by endogenous proteases and may be administered orally. Further, both enantiomers have similar effects on gramicidin (gA) gating. The similarity of the GsMTx4 and D-GsMTx4 effects is difficult to reconcile with traditional mechanisms for peptide-protein interactions, which involve stoichiometric, sterically well-defined, binding reactions. The changes in gA channel function are readily explained by altered bilayer properties, which alter the organization in the local environment of the channel and thus the free energy difference for the gA monomer þdimer equilibrium (Lundbæk et al., *J. Gen. Physiol.* 104, 645673 (1994); Hwang et al., *Biochemistry* 42, 1364613658 (2003); Lundbæk et al., *J. Gen. Physiol.* 123, 599621 (2004)).

Although the conformational changes underlying SAC gating are different from those underlying gA channel gating, the similar effects of GsMTx4 and D-GsMTx4 on SACs, and the ability of GsMTx4 to modify SACs from different tissues, suggests that the mode of action is the same—altered local bilayer mechanics. The efficacy of the D form of GsMTx4 is important for clinical applications. Because GsMTx4 can inhibit cardiac arrhythmias (Bode et al., *Nature* 409, 35-36, 2001) and D peptides are resistant to proteolysis, oral administration of the D-peptide, for example, can be used to treat arrhythmias. In one embodiment, this peptide can be locally applied during catheterization procedures to reduce arrhythmias.

The following examples describe the various embodiments of this invention. These examples are illustrative and are not intended to be restrictive.

EXAMPLE 1

Figure 4:
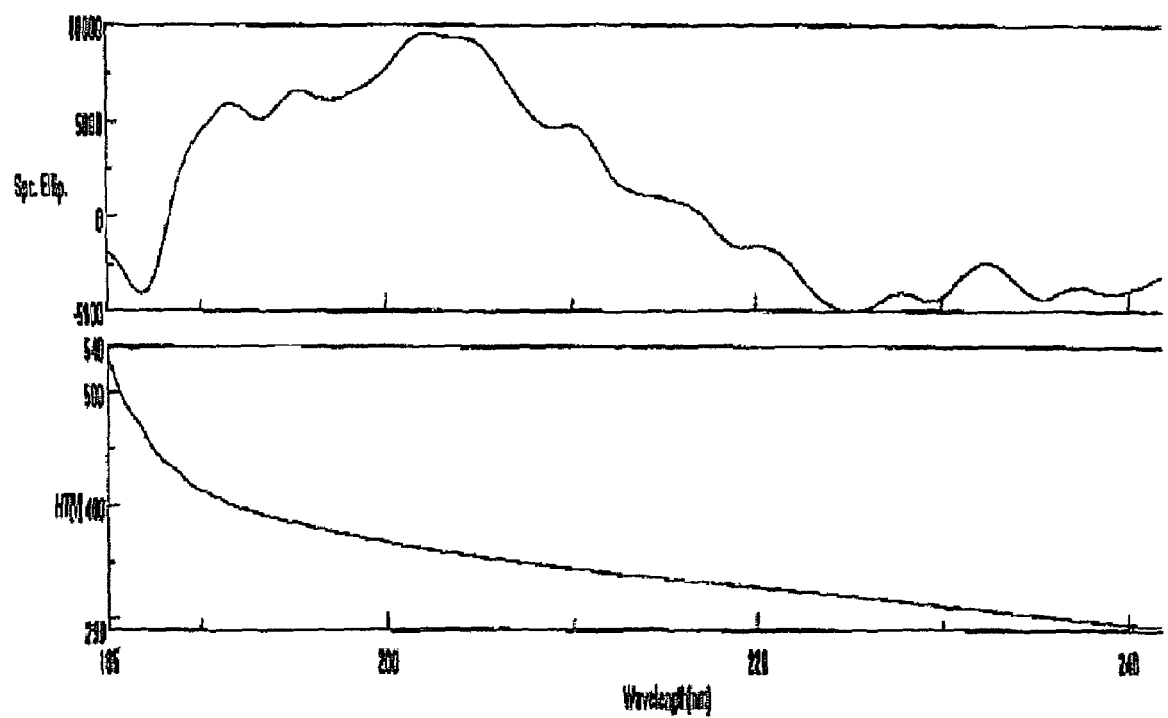
FIG. 4 is a representation of the CD spectrum of GsMTx4.

This example describes the synthesis of D-GsMTx-4. The linear sequence of GsMTx4 having D amino acids was synthesized by SynPep. Purification and folding was performed as described for the L-form (Ostrow et al., *Toxicon*, 42, 263-274, 2003). The material (70% pure) (125 mg was dissolved in water and insoluble material was removed by centrifugation. The peptide was purified by RP-HPLC (reverse phase-high-performance liquid chromatography) (Zorbax 300 SB-C18, 9.4×250 mm column) with a 20% to 45% acetonitrile-water gradient, containing 0.1% triflouroacetic acid, at a flow rate of 3 ml/min (Trudelle et al., *Int. J. Pept. Protein Res.* 30, 163-169 1987). Elution was monitored at 220 and 280 nm; the desired peptide fractions were identified by MALDI-TOF (matrix-assisted laser desorption/ionisation-time of flight), pooled and evaporated to dryness. The purified peptide (200 μg) was dissolved in 800 μl water plus 100 μl 1M Tris at pH 8.0. For folding, 50 μl of reduced glutathione (5 mM; Sigma), and 50 μl of oxidized glutathione (0.5 mM; Sigma) were added, and incubated for 24 h at room temperature. The reaction was terminated with 1 μl concentrated phosphoric acid. The folded peptide was purified with the gradient and detection described above using a C18 column (5 mm, 40×250 mm) at a flow rate of 1 ml/min (Trudelle et al., *Int. J. Pept. Protein Res.* 30, 163-169 1987). The MALDI-TOF and retention time on analytical HPLC for D-GsMTx4 was identical to GsMTx4. The circular dichroism spectrum of 10 mM enGsMTx4 in 5 mM phosphate buffer at pH 7.4 was inverted relative to GsMTx4 (Ostrow et al., *Toxicon* 42, 263-274, 2003) and is shown in FIG. 4.

EXAMPLE 2

This example describes the analysis of SACs in cultured cells

Methods

Primary reactive rat astrocytes cultures (passages 4 to 10) were prepared as previously described. Primary cultures of chick heart cells were prepared from 11-day-old embryos as previously described (Bett et al., *J. Membr. Biol.* 173, 237-254, 2000).

Outside-out patches were formed using pipettes containing 140 mM KCl, 2 mM MgCl2, 10 mM HEPES and 0.5 mM EGTA (as Kþ salts). SAC currents were recorded using an Axopatch 200B patch clamp, with pClamp9 software and a Digidata 1322A acquisition system (Axon Instruments). Pressure was applied to the patch pipette with an HSPC-1 pressure clamp, and the patch was perfused using an ALA MP285 perfusion system (ALA Scientific Instruments). GsMTx4 or analog was dissolved in the perfusion solution: 140 mM NaCl, 10 mM Na-HEPES, 5 mM KCl, and 1 mM MgCl2. All experiments were repeated 0.2-3 times.

Fluorescence measurements were performed as described by Ladokhin et al. (*Anal. Biochem.* 285, 235245, 2000) with an AMJNCO-Bowman Series 2 spectrofluorimeter. The excitation and emission wavelengths were 280 nm (8 nm band pass, 08 polarizer) and 346 nm (16 nm band pass, 908 polarizer). Large unilamellar vesicles of egg lecithin (Avanti Polar Lipids) were formed by extrusion. Tryptophan (Sigma) and GsMTx4 titration experiments were performed in 8 mM phosphate buffer containing 1 mM EGTA at pH 7. Three spectra were collected at each lipid concentration with both tryptophan and GsMtx4 (both at 30μM). After background subtraction, the mean fluorescence intensity at each lipid concentration was corrected for vesicle scattering (Ladokhin et al., *Anal. Biochem,* 285, 235245, 2000) and normalized to the zero lipid fluorescence intensity. The results are reported assuming a vesicle diameter of 130 nm, and area per lipid in the monolayer of 0.7 nm2.

Results

The results are shown in FIGS. 1a and 1b. FIG. 1a shows that ensemble-averaged SAC currents from a single outside-out astrocyte patch in the absence and presence of 5 mM GsMTx4. FIG. 1b shows average patch currents as a function of pressure in the absence and presence of 5 μM GsMTx4 (2 patches, mean ^ s.e.m.) shows that pressure can overcome peptide inhibition. The stimulus is near saturation at the highest pressure attainable without lysis. GsMTx4 suppressed the average inward current by 80%, but the open state dwell time distribution was not affected (data not shown). c, Single-channel currents from a chick heart cell, the outside-out patch shows mild rectification in the absence of GsMTx4. d, GsMTx4 reduces average currents in the chick heart cell outside-out patch. Control (black trace) and 5 mM GsMTx4 (red trace) show inhibition, that is slightly voltage dependent, reducing inward currents by 70% and outward currents by 90%. Histograms of unitary current amplitude showing no change in outward current amplitude (left) (þ 50 mV pipette potential: control, 1.10 pA; 5mM GsMTx4, 1.08 pA), but a 10% reduction in the inward current amplitude (right) (250 mV pipette potential: control, 1.74 pA; 5mM GsMTx4, 1.58 pA).

We have also observed that when CHO cells were transfected to express TRPC1, GsMTx4 inhibited stretch activated channels.

GsMTx4 inhibits ubiquitous cationic SACs in a variety of vertebrate cell types (200-600 nM, for example, chick heart, rat astrocytes and skeletal muscle, and human smooth muscle) (Gottlieb et al., *Current Drug Targets—CNS & Neurological Disorders* 3:287-295, 2004) despite the fact that they have different kinetic properties and presumably different structure. As shown in FIGS. 1a and 1b, it inhibits channel activity when applied to the extracellular face of the cell membrane by increasing the membrane tension required for activation, suggesting that GsMTx4 acts as a gating modifier. In the presence of GsMTx4 (FIGS. 1c-e), the inward currents were reduced, 10% with no observable effect on outward currents. While not intending to be bound by any particular theory, it is believed, based on predictions using the Poisson-Boltzmann models, that this effect is seen when GsMTx4 is located within about 1.5 nm of the channel vestibule.

To determine if GsMTx4 functions by altering bilayer properties, using the tryptophan fluorescence (Ladokhin et al., supra) of GsMTx4, we measured its binding to large unilamellar lipid vesicles. The partition coefficient, defined as $([GsMTx4]_{bil}/[Lipid])/([GsMTx4]_{aq}/[H_2O])$ (where the subscripts denote the bilayer and aqueous phases, respectively, for example see White et al., *Methods Enzymol.* 295, 62-87, 1998), was ~3×10$^5$ corresponding to an adsorption coefficient of 10$^{-3}$ cm (defined as $^2_{bil}/[GsMTx4]_{aq}$, where $^2_{bil}$ denotes the surface density, in moles per unit area). GsMTx4 thus binds avidly to lipid bilayers: at 500 nM, (the effective KD for gating) the GsMTx4:lipid ratio in the outer leaflet is,1:300, meaning that the peptide concentration within a 1 nm thick layer of membrane at the bilayer/solution interface is 104-fold higher than the bulk concentrations. This has two implications. First, the intrinsic affinity between a lipid-bound GsMTx4 and the channel could be quite modest and yet account for the observed KD (Kim et al., *Biophys. J.* 60, 135148, 1991). Second, the mean surface density of GsMTx4 is sufficiently high that fast exchange (50 ms) between the bulk bilayer and the lipids adjacent to the channel can alter the local (and global) bilayer mechanical properties. The apparent association and dissociation rates for SAC effects ($K_a \approx 10^6$ M$^{-1}$ s$^{-1}$, $K_D \approx 0.2$ s$^{-1}$) are consistent with such a fast exchange (as well as slower, more specific binding).

EXAMPLE 3

Figure 2:
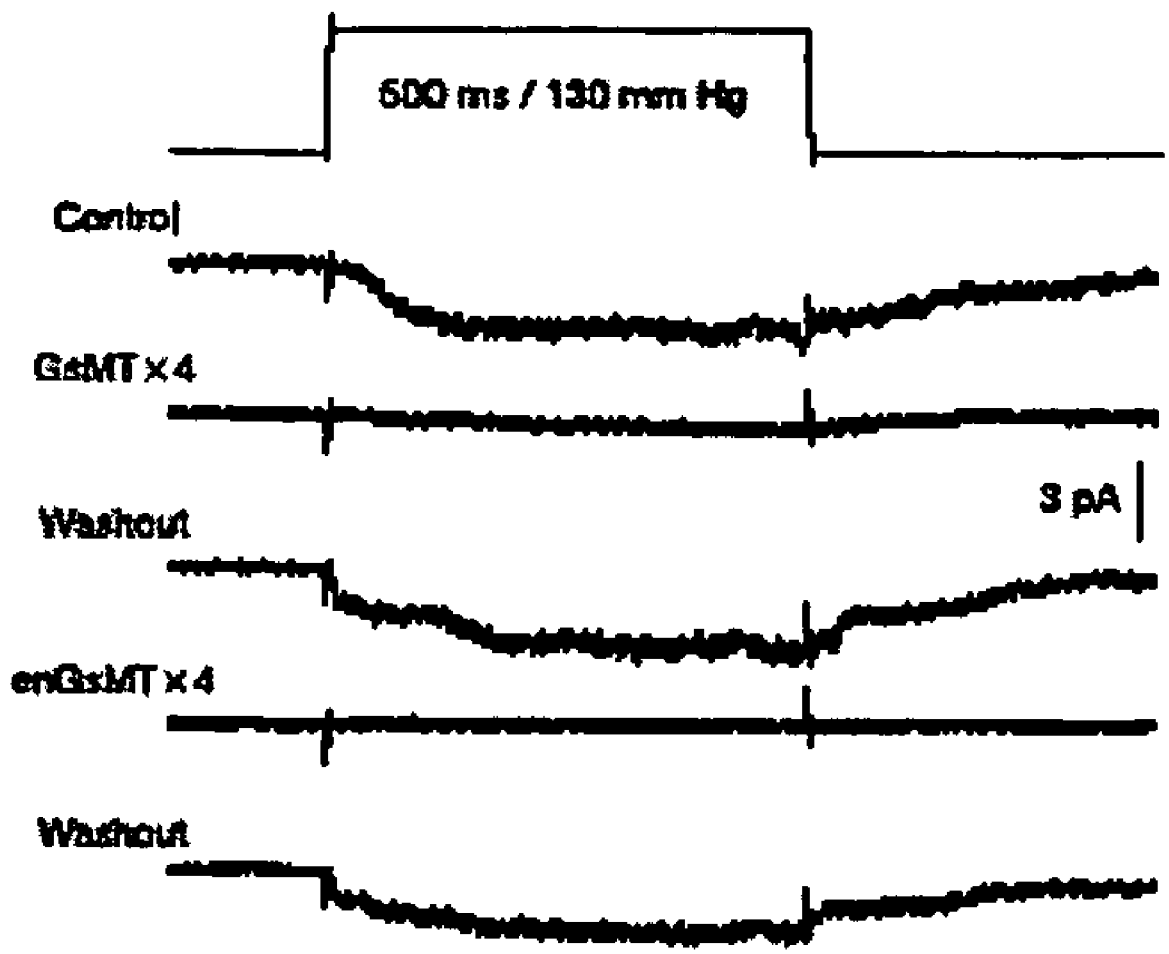
FIG. 2 is a representation of 5 μM GsMTx4 and D-GsMTx4 on the averaged current from a rat astrocyte outside-out patch.

To examine whether GsMTx4 could alter SAC function through a purely bilayer-dependent mechanism, we synthesized D-GsMTx4 from D amino acids as described in Example 1, and tested its effect on SACs. Except for its optical properties, enGsMTx4 is indistinguishable from wild-type GsMTx4. The results shown in FIG. 2, indicate that both inhibit SACs. The effect seen with D-GsMTx4 was surprising because traditional models of protein-protein interaction are of the lock and key style, in which there are close steric interactions. A mirror image D enantiomer would not fit in the same lock as the L enantiomer, but in this case the effect is the same. The lack of chirality in protein-protein peptide effects is rare The D-forms inhibit SACs with similar efficacy to GsMTx4 (FIG. 2). Thus, GsMTx4 is unlikely to alter SAC gating by a lock-and-key mechanism, but, judging by the effects on conductance (FIG. 1e), the peptide is in close proximity to the channel.

EXAMPLE 4

This example demonstrates that L-GsMTx-4 and D-GsMTx-4 similarly affect the constitutive properties of lipid bilayers.

The effect of L-GsMTx-4 on gA gating was first determined. gA channels are dimers formed by the transbilayer association of monomers in opposing monolayers (O'Connell et al., *Science* 250, 1256-1259, 1990). Channel formation is generally associated with local bilayer thinning, which makes gA monomer ⇌ dimer equilibrium and thus the channel lifetime and appearance rate sensitive to bilayer thickness, elastic moduli and curvature stress. Thus, if GsMTx4 binds to the lipid bilayer, one would expect it to also alter the lipid packing adjacent to the channel and thus the gA gating kinetics and, because it is cationic decrease the channel current.

Figure 3:
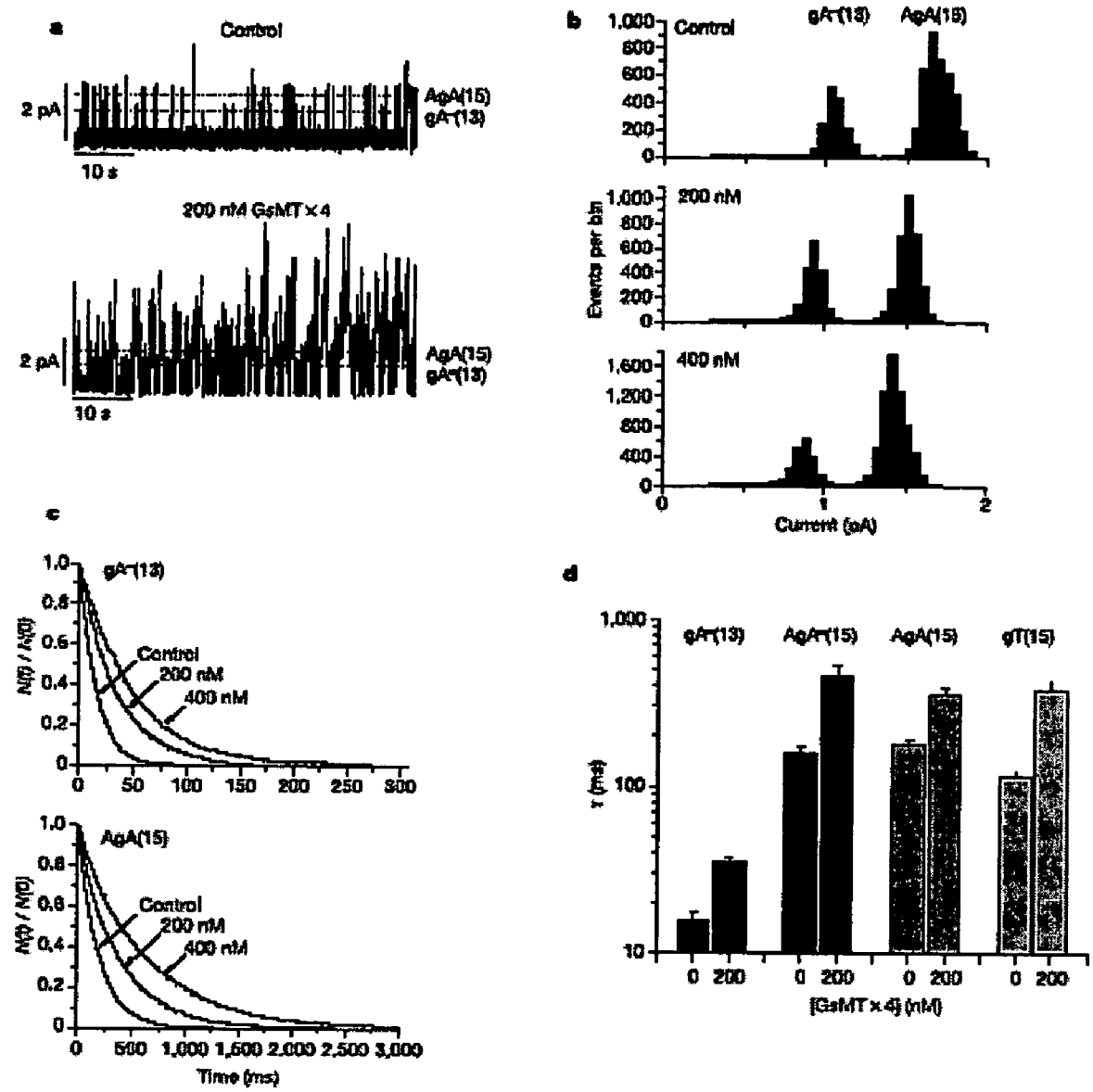
FIG. 3 is a representation of the effect of GsMTx4 on gA channels. a, Current traces before and after addition of 200 nM GsMTx4 to both sides of a bilayer doped with chain-shortened des-Val 1-Gly 2-gA (gA2(13)) and [Ala 1]gA (AgA(15)) (numbers in parenthesis denote number of residues in the sequence): gA2 is the enantiomer of gA20. b, c, Single-channel currents (b) and lifetimes (c) as a function of GsMTx4 concentration (see Methods). d, Average lifetime (t) as a function of channel length, helix sense and identity of the aromatic at the channel/solution interface. gA2(13) and AgA(15) as above, AgA2(15) is [D-Ala 1]gA2, gT is [Tyr9,11,13,15]gA (ref. 21). 200 nM GsMTx4; columns and error bars denote mean±s.d. (n≧3).

FIG. 3 shows that GsMTx4 increases the channel activity of gA (and gA analogues of different length) (FIG. 3a), and reduces the single-channel current (FIG. 3b). The increased activity results from a 10-25-fold increase in appearance rate, and an approximately 2-fold increase in open channel lifetime (FIG. 3c), with channels formed by the shorter gA analogs being more sensitive than those formed by the longer analogs. These changes in channel function do not result from specific binding of GsMTx4 to gA. First, the changes in channel lifetime do not depend on the channels' helix sense, as shown using a pair of enantiomeric gA analogues (FIG. 3d). Second, GsMTx4 most likely resides at the bilayer/solution interface, meaning that any channel-peptide interactions would be expected to involve the four tryptophan residues at the channel/solution interfaces; but channels formed by a tryptophan≧tyrosine substituted gA are affected similarly as other gA channels (FIG. 3d). Third, L-GsMTx4 and D-GsMTx4 similarly modulate gA activity, as 400 nM D-GsMTx-4 increases the channel appearance rates 10-fold and the lifetime 4-fold.

These results indicate that D-GsMTx4 is at least as potent and may be more potent than L-GsMTx-4 (FIG. 2) and it appears that D-GsMTx4 exerts its effects on gA channels (at the same concentrations that affect SACs)1 by altering the lipid packing at the bilayer/solution/channel interface.

This invention has been described through examples presented above. Routine modifications to the methods and compositions presented herein will be apparent to those skilled in the art and are intended to be within the scope of the claims appended hereto.

We claim:

1. A peptide selected from the group-consisting of the sequence of SEQ ID NO:1 and variants thereof, wherein the variants can block stretch activated channels, have a sequence which comprises an inhibitor cysteine knot (ICK) motif, are resistant to proteolysis, and wherein each variant has at least one conservative amino acid substitution in the sequence of SEQ ID NO:1.

2. The peptide of claim 1, wherein the peptide is present in a pharmaceutically acceptable carrier.

3. A method of reducing cardiac arrhythmia comprising administering the peptide of claim 1 in a pharmaceutically acceptable carrier in an amount effective to reduce cardiac arrhythmia to a patient in need of treatment.

4. The method of claim 1, wherein the cardiac arrhythmia occurs during catheterization.

5. A method of blocking stretch-activated channels in a cell comprising the step of contacting the cell with a sufficient amount of the peptide of claim 1 effective for blocking stretch activated channels in the cell.

6. The method of claim 5, wherein the cell is a myocardial cell.

7. The method of claim 5, wherein the cell is an astrocyte.

8. The method of claim 5, wherein the cell is a myocyte.

9. The method of claim 5, wherein the cell is a glioma cell.

10. The method of claim 5, wherein the peptide is used for blocking stretch activated channels during catheterization.

11. The method of claim 10, wherein the cell is present in an individual diagnosed with muscular dystrophy.

* * * * *

UNITED STATES PATENT AND TRADEMARK OFFICE
CERTIFICATE OF CORRECTION

PATENT NO. : 7,259,145 B2 Page 1 of 1
APPLICATION NO. : 11/176745
DATED : August 21, 2007
INVENTOR(S) : Sachs et al.

It is certified that error appears in the above-identified patent and that said Letters Patent is hereby corrected as shown below:

On title page, Item [75] In the list of Inventors, page 1, the third Inventor, "Phillip Gottlieb" should read --Philip Gottlieb--.

Signed and Sealed this

Sixteenth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,259,145 B2 Page 1 of 1
APPLICATION NO. : 11/176745
DATED : August 21, 2007
INVENTOR(S) : Sachs et al.

It is certified that error appears in the above-identified patent and that said Letters Patent is hereby corrected as shown below:

Column 1 Line 3 and 4 - insert at end of first paragraph:

--This invention was made with Government support under Grant No. HL054887 awarded by the National Institutes of Health. The Government has certain rights in the invention--.

Signed and Sealed this

Twenty-sixth Day of May, 2009

JOHN DOLL
*Acting Director of the United States Patent and Trademark Office*